US011389139B2

(12) United States Patent
Yang et al.

(10) Patent No.: US 11,389,139 B2
(45) Date of Patent: Jul. 19, 2022

(54) ECHO WINDOW ARTIFACT CLASSIFICATION AND VISUAL INDICATORS FOR AN ULTRASOUND SYSTEM

(71) Applicant: Verathon Inc., Bothell, WA (US)

(72) Inventors: Fuxing Yang, Bothell, WA (US); Joon Hwan Choi, Bothell, WA (US)

(73) Assignee: VERATHON INC., Bothell, WA (US)

( * ) Notice: Subject to any disclaimer, the term of this patent is extended or adjusted under 35 U.S.C. 154(b) by 815 days.

(21) Appl. No.: 16/213,418

(22) Filed: Dec. 7, 2018

(65) Prior Publication Data
US 2019/0183462 A1 Jun. 20, 2019

Related U.S. Application Data

(60) Provisional application No. 62/608,134, filed on Dec. 20, 2017.

(51) Int. Cl.
A61B 8/08 (2006.01)
A61B 8/14 (2006.01)
(Continued)

(52) U.S. Cl.
CPC .......... A61B 8/5223 (2013.01); A61B 5/7267 (2013.01); A61B 8/085 (2013.01);
(Continued)

(58) Field of Classification Search
CPC ... A61B 8/5223; A61B 5/7267; A61B 8/5292; A61B 8/5269; A61B 8/145; A61B 8/085; A61B 8/463; A61B 5/4325; A61B 5/4381; G16H 50/20; G16H 30/40; G06T 5/001; G06T 7/0012; G06T 2207/20081; G06T 2207/10132; G06T 2207/20084;
(Continued)

(56) References Cited

U.S. PATENT DOCUMENTS 4,835,712 A * 5/1989 Drebin .................... G06T 17/00
345/423
6,398,733 B1 6/2002 Simopoulos et al.
(Continued)

FOREIGN PATENT DOCUMENTS

EP 3048980 B1 8/2017

OTHER PUBLICATIONS

International Search Report and Written Opinion issued in corresponding International Application No. PCT/US2018/064483, dated Jan. 31, 2019, 12 pages.

*Primary Examiner* — Bo Joseph Peng
(74) *Attorney, Agent, or Firm* — Snyder, Clark, Lesch & Chung, LLP

(57) ABSTRACT

A method for providing artifact detection and visualization during ultrasound image collection is performed by a processor in an ultrasound system. The method includes receiving ultrasound image data from an ultrasound probe, detecting areas with artifacts in the ultrasound image data, classifying the areas with artifacts into one of a plurality of available artifact classes, generating an indication of the areas with artifact for an ultrasound-based image, wherein the indications include a designation of the artifact class, and presenting to an operator the ultrasound-based image and the indication of the areas with artifacts.

20 Claims, 12 Drawing Sheets

(51) Int. Cl.
  *A61B 8/00* (2006.01)
  *G06N 3/08* (2006.01)
  *G06K 9/62* (2022.01)
  *G06T 7/00* (2017.01)
  *G06N 3/04* (2006.01)
  *G16H 50/20* (2018.01)
  *G06T 5/00* (2006.01)
  *G16H 30/40* (2018.01)
  *A61B 5/00* (2006.01)

(52) U.S. Cl.
  CPC ............ *A61B 8/145* (2013.01); *A61B 8/463* (2013.01); *A61B 8/5269* (2013.01); *A61B 8/5292* (2013.01); *G06K 9/627* (2013.01); *G06K 9/628* (2013.01); *G06N 3/04* (2013.01); *G06N 3/0454* (2013.01); *G06N 3/08* (2013.01); *G06T 5/001* (2013.01); *G06T 7/0012* (2013.01); *G16H 30/40* (2018.01); *G16H 50/20* (2018.01); *A61B 5/4325* (2013.01); *A61B 5/4381* (2013.01); *G06T 2207/10132* (2013.01); *G06T 2207/20081* (2013.01); *G06T 2207/20084* (2013.01); *G06T 2207/30168* (2013.01)

(58) Field of Classification Search
  CPC ........ G06T 2207/30168; G06N 3/0454; G06N 3/08; G06N 3/04; G06K 9/628; G06K 9/627
  See application file for complete search history.

(56) References Cited

U.S. PATENT DOCUMENTS

| | | |
|---|---|---|
| 7,536,044 B2 | 5/2009 | Zhou et al. |
| 7,648,460 B2 | 1/2010 | Simopoulos et al. |
| 7,747,054 B2 | 6/2010 | Zhou et al. |
| 7,822,252 B2 | 10/2010 | Bi et al. |
| 7,876,934 B2 | 1/2011 | Georgescu et al. |
| 8,885,926 B2 | 11/2014 | Seung et al. |
| 9,538,925 B2 | 1/2017 | Sharma et al. |
| 9,672,471 B2 | 6/2017 | Boyden et al. |
| 2007/0055153 A1* | 3/2007 | Simopoulos ........... G16H 30/40 600/437 |
| 2013/0123635 A1* | 5/2013 | Wegner ................ A61B 8/5207 600/447 |
| 2014/0052001 A1 | 2/2014 | Ionasec et al. |
| 2015/0379700 A1 | 12/2015 | Kamiyama et al. |
| 2016/0048972 A1 | 2/2016 | Kam et al. |
| 2016/0345931 A1 | 12/2016 | Xu et al. |
| 2016/0350620 A1 | 12/2016 | Rao et al. |
| 2019/0005644 A1* | 1/2019 | Yaguchi .................... G06T 7/44 |

* cited by examiner

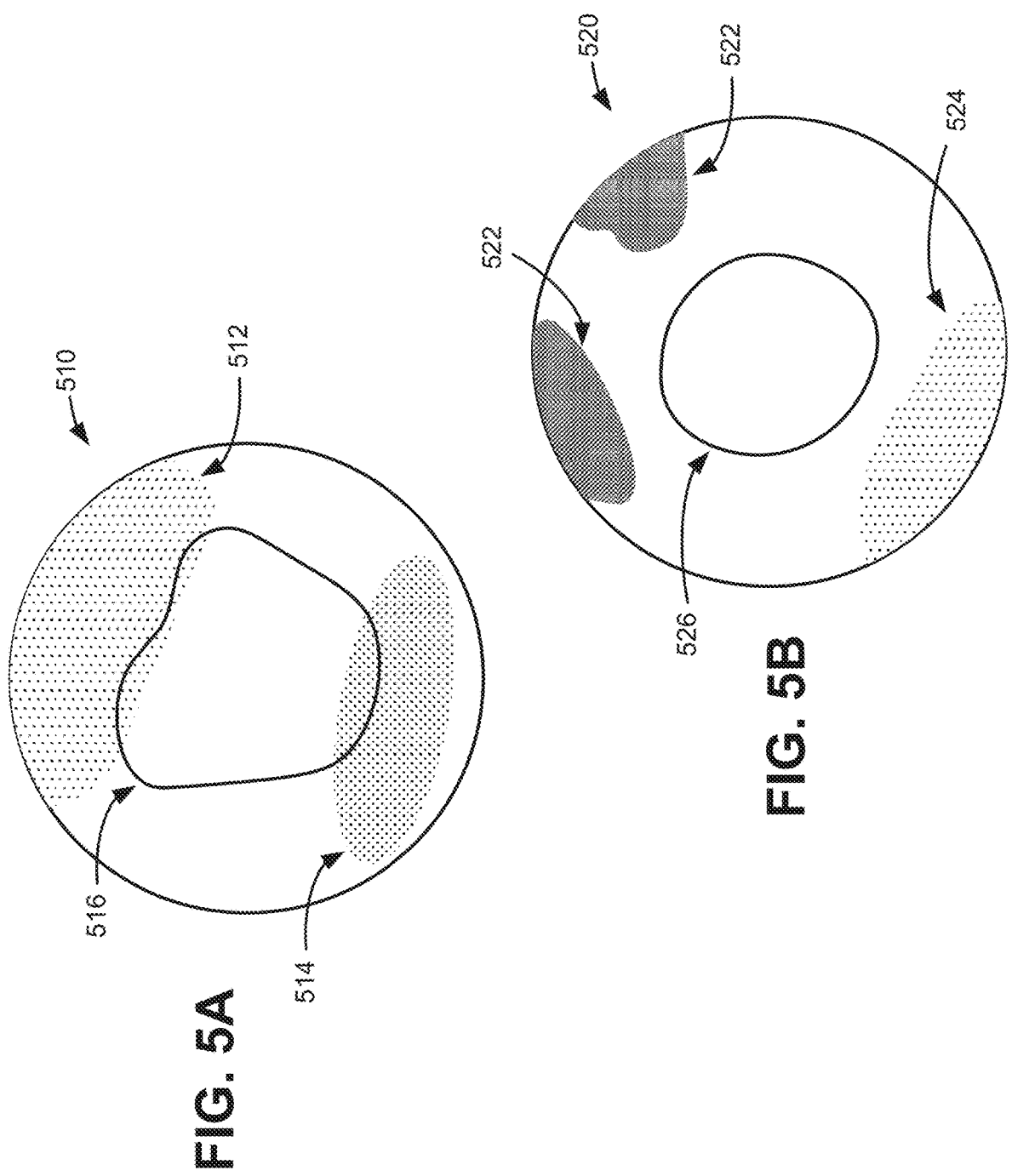

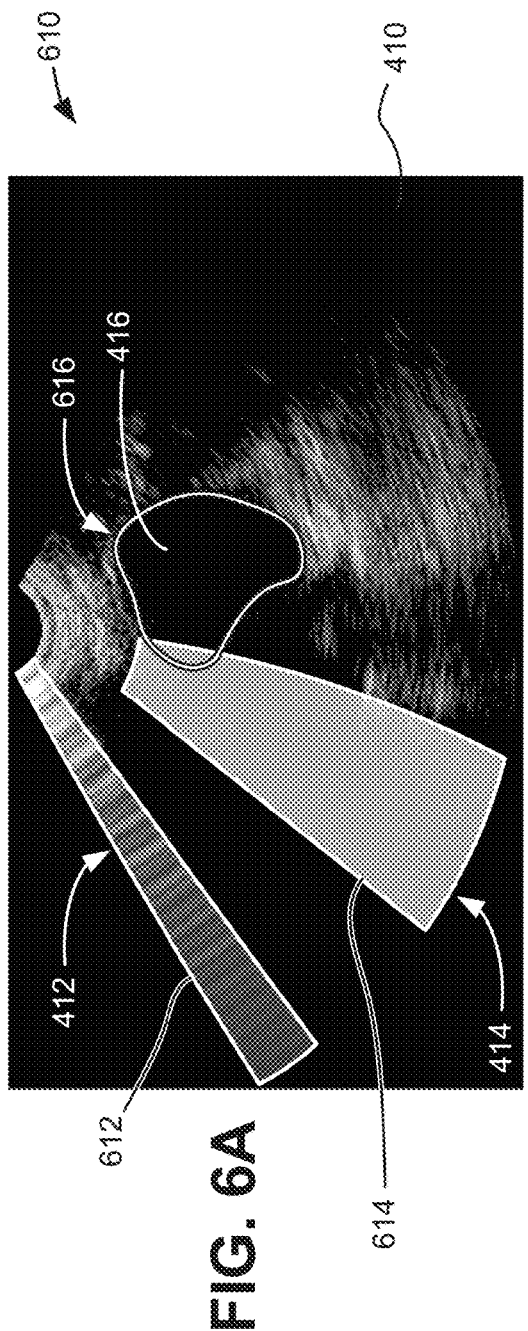
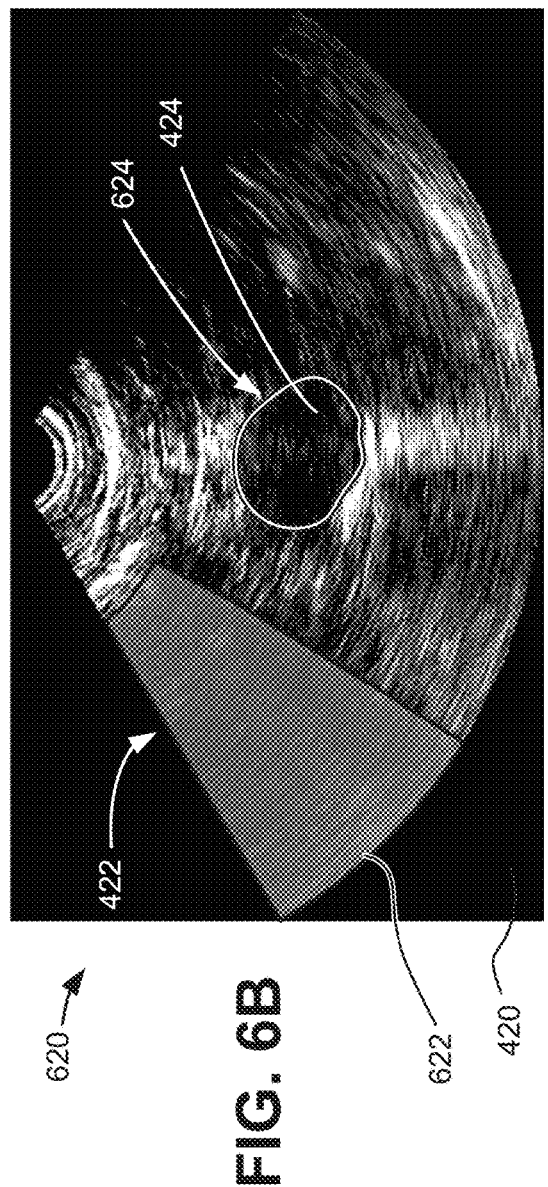
FIG. 6A
FIG. 6B

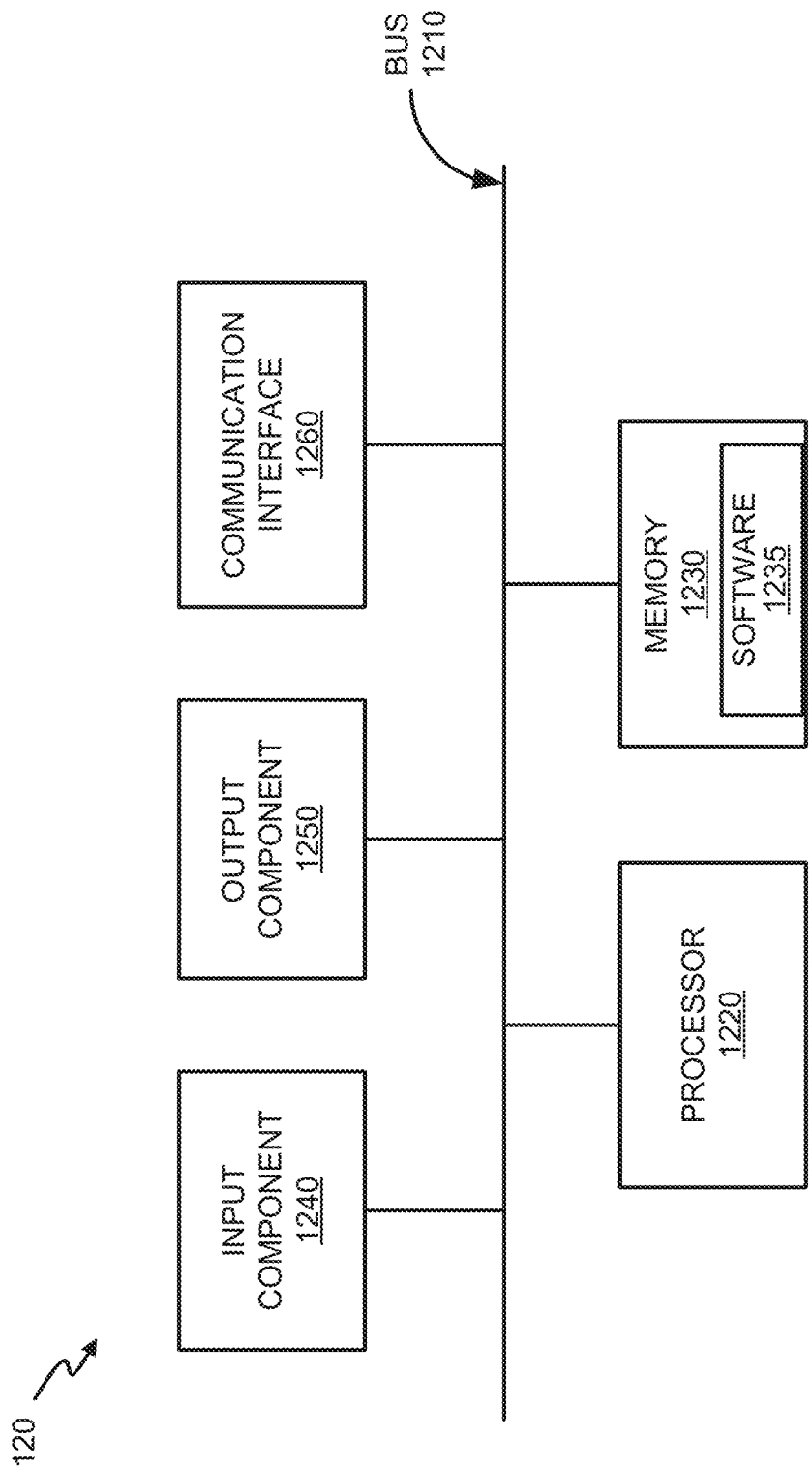

ECHO WINDOW ARTIFACT CLASSIFICATION AND VISUAL INDICATORS FOR AN ULTRASOUND SYSTEM

CROSS-REFERENCE TO RELATED APPLICATION

This application claims priority under 35 U.S.C. § 119, based on U.S. Provisional Patent Application No. 62/608,134 filed Dec. 20, 2017, the disclosure of which is hereby incorporated by reference.

BACKGROUND

Ultrasound scanners are typically used to identify a target organ or another structure in the body and/or determine features associated with the target organ/structure, such as the size of a structure or the volume of fluid in an organ. Obtaining an adequate quality of ultrasound images can be challenging even for experienced operators.

Using ultrasound imaging technology on human subjects, operators frequently notice unwanted image artifacts from different sources, such as the pubic bone, insufficient gel, bowel gas, etc. These artifacts can hide important information needed to make accurate organ measurements and corresponding clinical decisions. An experienced operator may be able to make adjustments to avoid unwanted artifacts, such as moving a probe to avoid blocking bones or applying more gel. However, for most operators, an automated indication of an error type can help the operator make correct adjustments more quickly and effectively to obtain better imaging of a target organ.

BRIEF DESCRIPTION OF THE DRAWINGS

FIGS. 5A and 5B are sample C-mode images that may be generated by the data acquisition unit of FIG. 2;

FIGS. 6A and 6B are sample visualizations applied to the B-mode images of FIGS. 4A and 4B;

FIG. 12 is a diagram illustrating exemplary components of a base unit in the system of FIG. 1.

DETAILED DESCRIPTION OF THE PREFERRED EMBODIMENTS

The following detailed description refers to the accompanying drawings. The same reference numbers in different drawings may identify the same or similar elements.

Implementations described herein utilize machine learning to classify artifact information from B-mode ultrasound echoes into simple visual indications within an ultrasound imaging system, to assist in providing better aiming and more accurate quantitative analysis. According to one example, a convolutional neural network can be used to generate a probability map corresponding to the shadows from different sources inside B-mode images. Simple visual indications can then be constructed from the maps for the operator to make adjustments in order to achieve better image quality and better measurement accuracy.

In one implementation, a method for providing artifact detection and visualization during ultrasound image collection may be performed by a processor in an ultrasound system. The method may include receiving ultrasound image data from an ultrasound probe, detecting areas with artifacts in the ultrasound image data, classifying the areas with artifacts into a class selected from a group of available artifact classes, generating an indication of the areas with an artifact for an ultrasound-based image, wherein the indications include a designation of the selected class, and presenting to an operator the ultrasound-based image and the indication of the areas with artifacts. As described further herein, an ultrasound-based image may generally include a B-mode image, a C-mode image, or another type of image derived from ultrasound data.

Figure 1:
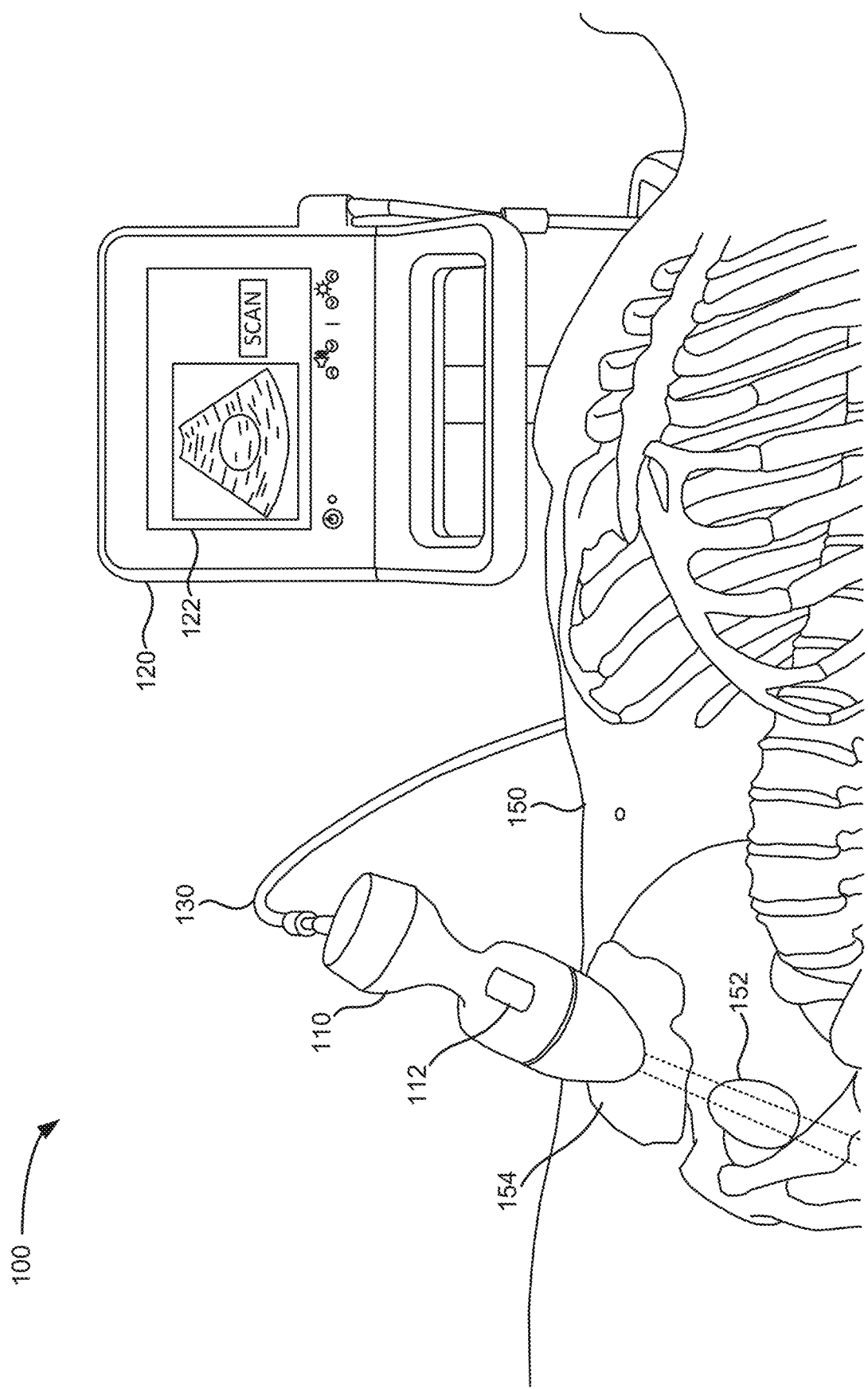
FIG. 1 is a schematic of a scanning system in which systems and methods described herein may be implemented.

FIG. 1 is a schematic of a scanning system 100 in which systems and methods described herein may be implemented. Referring to FIG. 1, scanning system 100 includes a probe 110, a base unit 120, and a cable 130.

Probe 110 includes a handle portion, a trigger, and a nose (or dome) portion. Medical personnel may hold probe 110 via the handle and press trigger 112 to activate one or more ultrasound transceivers, located in the nose portion, to transmit ultrasound signals toward a target object of interest, which may include an organ (e.g., a bladder, an aorta, a kidney, etc.) or a non-organ structure (e.g., a catheter, a needle, or another medical device). For example, as shown in FIG. 1, probe 110 is located on pelvic area of patient 150 and over a target object of interest 152, which in this example is the patient's bladder.

The dome of probe 110 is typically formed of a material that provides an appropriate acoustical impedance match to an anatomical portion and/or permits ultrasound energy to be properly focused as it is projected into the anatomical portion. For example, an acoustic gel or gel pads, illustrated at area 154 in FIG. 1, may be applied to patient's skin over the region of interest (ROI) to provide an acoustical impedance match when the dome is placed against the skin.

Probe 110 includes one or more ultrasound transceiver elements and one or more transducer elements within the dome that transmit ultrasound energy outwardly from the dome, and receive acoustic reflections or echoes generated by internal structures/tissue within the anatomical portion. For example, the one or more ultrasound transducer elements may include a one-dimensional, or a two-dimensional array of piezoelectric elements that may be moved within the dome by a motor to provide different scan directions with respect to the transmission of ultrasound signals by the transceiver elements. Alternatively, the transducer elements may be stationary with respect to probe 110 so that the selected anatomical region may be scanned by selectively energizing the elements in the array.

Probe 110 may communicate with base unit 120 via a wired connection, such as via cable 130. In other implementations, probe 110 may communicate with base unit 120 via a wireless connection (e.g., Bluetooth, Wi-Fi, etc.). In each case, base unit 120 includes a display 122 to allow an operator to view processed results from an ultrasound scan, and/or to allow operational interaction with respect to the operator during operation of probe 110. For example, display 122 may include an output display/screen, such as a liquid crystal display (LCD), light emitting diode (LED) based display, or other type of display that provides text and/or image data to an operator. For example, display 122 may provide artifact visualizations overlaid on B-mode images to help determine the quality/accuracy of an ultrasound scan. Display 122 may also display two-dimensional or three-dimensional images of the selected anatomical region.

To scan a selected anatomical portion of a patient, the dome of probe 110 may be positioned against a surface portion of patient 150 as illustrated in FIG. 1 that is proximate to the anatomical portion to be scanned. The operator actuates the transceiver and transducer elements, causing the transceiver to transmit ultrasound signals into the body and receive corresponding return echo signals that may be at least partially processed by the transceiver to generate an ultrasound image of the selected anatomical portion. In a particular embodiment, the transceiver transmits ultrasound signals with the center frequency in a range that extends from approximately about two megahertz (MHz) to approximately 10 MHz or more.

In one embodiment, probe 110 may be coupled to a base unit 120 that is configured to generate ultrasound energy at a predetermined frequency and/or pulse repetition rate and to transfer the ultrasound energy to the transceiver. Base unit 120 also includes one or more processors or processing logic configured to process reflected ultrasound energy that is received by the transceiver to produce an image of the scanned anatomical region.

In still another particular embodiment, probe 110 may be a self-contained device that includes one or more microprocessors or processing logic configured within the probe 110 and software associated with the microprocessor to operably control the transceiver and transducer elements, and to process the reflected ultrasound energy to generate the ultrasound image. Accordingly, a display on probe 110 may be used to display the generated image and/or to view artifact visualizations and other information associated with the operation of the transceiver. In other implementations, the transceiver may be coupled to a general-purpose computer, such as a laptop or a desktop computer that includes software that at least partially controls the operation of the transceiver and transducer elements, and also includes software to process information transferred from the transceiver so that an image of the scanned anatomical region may be generated.

Figure 2:
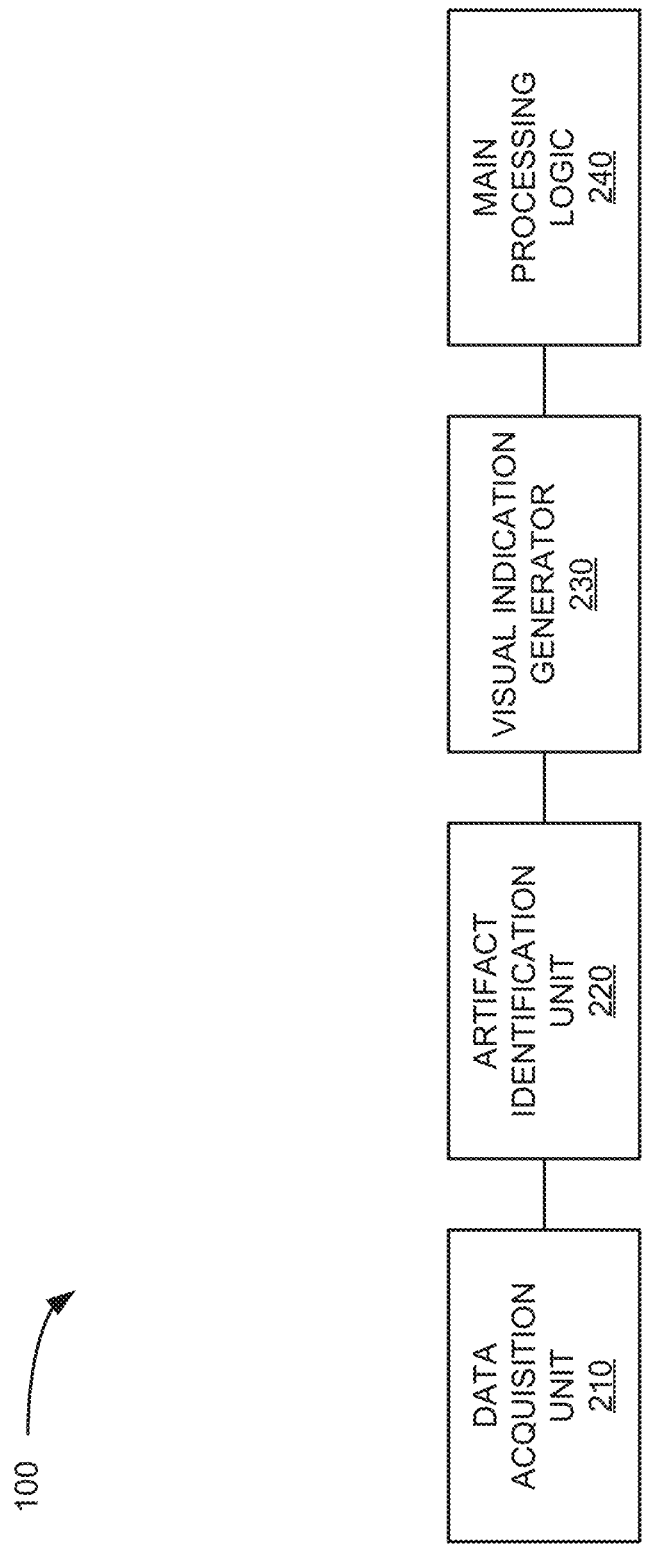
FIG. 2 is a block diagram of functional logic components implemented in the system of FIG. 1 in accordance with an exemplary implementation.

FIG. 2 is a block diagram of functional logic components implemented in system 100 in accordance with an exemplary implementation. Referring to FIG. 2, system 100 includes a data acquisition unit 210, an artifact identification unit 220, a visual indication generator 230, and main processing logic 240. In an exemplary implementation, data acquisition unit 210 may be part of probe 110 and the other functional units (e.g., artifact identification unit 220, visual indication generator 230, and main processing logic 240) may be implemented in base unit 120. Alternatively, data acquisition unit 210, artifact identification unit 220, visual indication generator 230, and main processing logic 240 may be implemented in probe 110. In other implementations, the particular units and/or logic may be implemented by other devices, such as via computing devices or servers located externally with respect to both probe 110 and base unit 120 (e.g., accessible via a wireless connection to the Internet or to a local area network within a hospital, etc.). For example, probe 110 may transmit echo data and/or image data to a processing system via, for example, a wireless connection (e.g., Wi-Fi or some other wireless protocol/technology) that is located remotely from probe 110 and base unit 120.

As described above, probe 110 may include a transceiver that produces ultrasound signals, receives echoes from the transmitted signals and generates image data based on the received echoes. Data acquisition unit 210 may include, for example, demodulation, decimation, log compression, and filtering sub-modules, to generate an image that can be presented for visualization by a human. A rotating transducer or transducer array with probe 110 may scan along multiple scan planes.

Figure 3C:
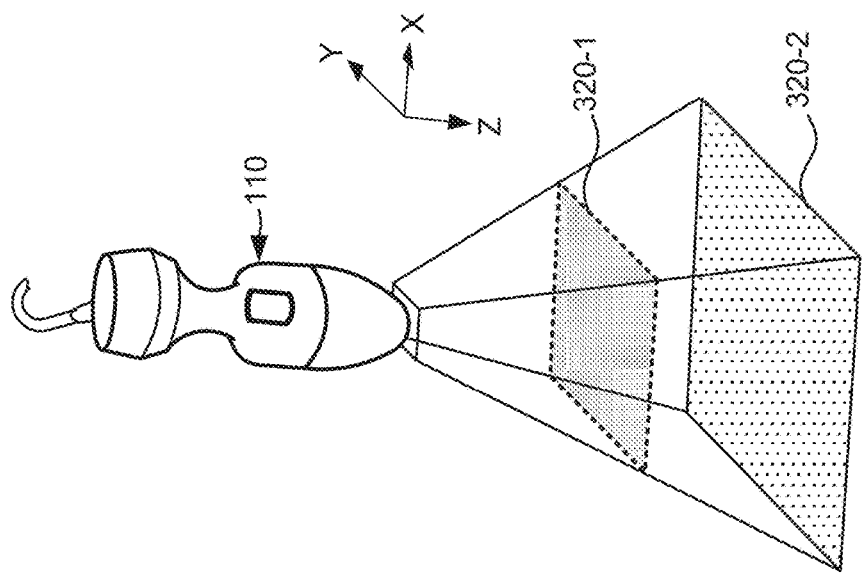
FIGS. 3A, 3B, and 3C are schematics illustrating exemplary B-mode and C-mode scanning planes, respectively, of the ultrasound probe of FIG. 1.
Figure 3B:
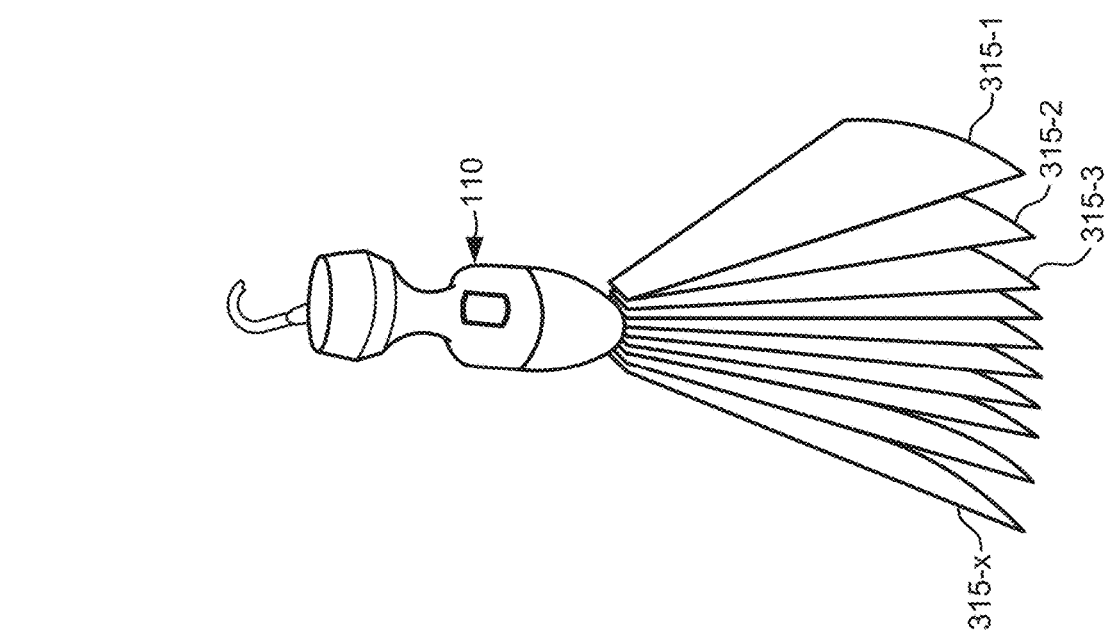
Figure 3A:
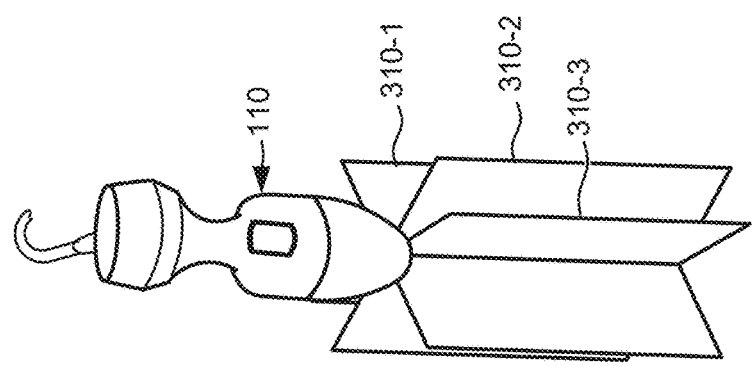

FIGS. 3A and 3B provide simplified illustrations of scan planes 310 (e.g., planes 310-1, 310-2, and 310-3) and 315 (e.g., planes 315-1, 315-2, 315-3, etc.) which may be employed by probe 110 to capture ultrasound images. Data acquisition unit 210 may use image data from one or more scan planes 310 or 315 to generate two-dimensional B-mode images, such as B-mode images 410 and 420 shown in FIGS. 4A and 4B, respectively. While three scan planes 310 and ten scan planes 315 are shown in FIGS. 3A and 3B, respectively, in practice, more scan planes are used to compile a comprehensive image of a target object. For example, dozens of scan planes may be used by some probes 110. In an exemplary implementation, data acquisition unit 210 obtains data associated with multiple scan planes corresponding to the region of interest in patient 150.

FIG. 3C provides a simplified illustration of C-mode image planes 320. C-mode images may generally include a representation oriented perpendicular to typical B-mode scan planes 310, for example. In one implementation, a C-mode image may include a cross-sectional image generated from ultrasound data of scan planes 310 or 315 at a particular depth, as indicated by plane 320-1. Thus, data acquisition unit 210 may use image data from a certain depth in each of scan planes 310 or 315 to generate a C-mode image. In another implementation, a C-mode image may include a 'shadowgram' or 'projection' of 3D ultrasound data onto an 'XY' plane, where Z axis represents depth, as indicated by plane 320-2. C-mode images may be presented as an ultrasound image or as a cartoon-like graphic. Simplified illustrations of C-mode images 510 and 520 are shown in FIGS. 5A and 5B, respectively.

Referring again to FIG. 2, artifact identification unit 220 may perform pre-processing of an image and detect in real time if ultrasound artifacts (e.g., false-positive echoes or false-negative echoes due to shadows, air/poor coupling, bowel gases, and other types of interference) are present in an echo window, which may be a B-mode image, a C-mode image, or another type of ultrasound image. For example, artifact identification unit 220 may receive an input image from data acquisition unit 210 (e.g., any of images 410, 420, 510, 520, etc.) and detect features in the echo window that are indicative of ultrasound artifacts. As described further herein, artifact identification unit 220 may analyze B-mode image data, C-mode image data, or other types of image data using a multi-class artifact categorization algorithm to recognize one or more types of artifacts, such as shadows, gases, air-interfaces, etc.

Figure 4A:
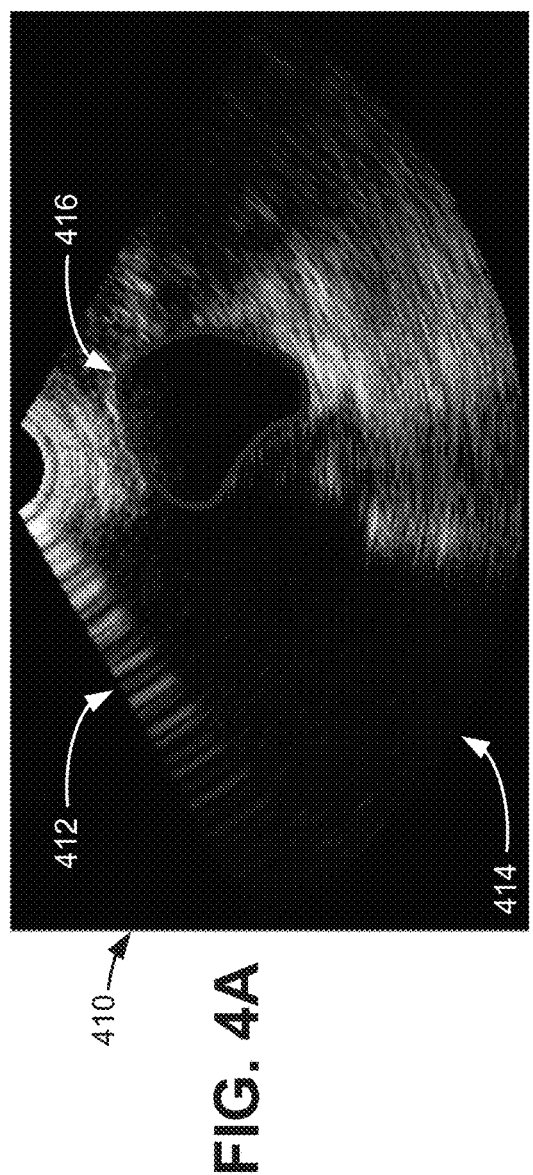
FIGS. 4A and 4B are sample B-mode images that may be generated by the data acquisition unit of FIG. 2.
Figure 4B:
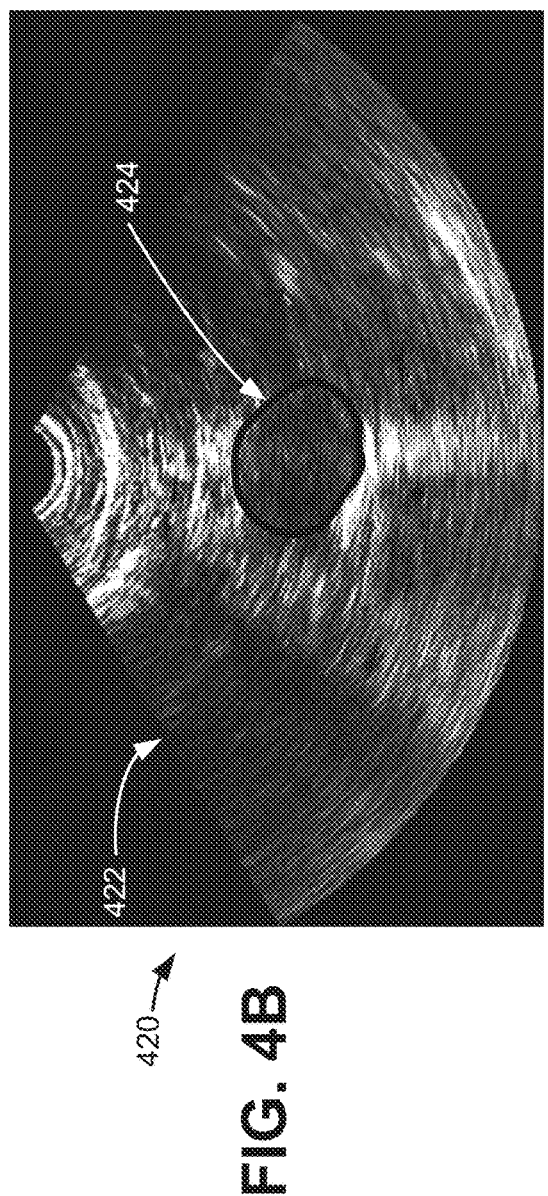

For example, referring to FIG. 4A, artifact identification unit 220 may detect an air scan area 412 and a pubic bone shadow 414 within B-mode image 410 that targets a bladder 416. As another example, referring to FIG. 4B, artifact identification unit 220 may detect an area of bowel gas 422 within B-mode image 420 that targets an aorta 424. Referring to FIG. 5A, C-mode images are generated from a compilation of B-mode images. Artifact identification unit 220 may similarly detect an air scan area 512 and a pubic bone shadow 514 within a C-mode image 510 that targets a bladder 516 (although air scan area 512 and pubic bone shadow 514 may not typically be shown in a conventional C-mode image). Referring to FIG. 5B, artifact identification unit 220 may detect areas of bowel gas 522 and an air scan area 524 within a C-mode image 520 that targets an aorta 526. While artifacts such as air scan area 412, pubic bone shadow 414, bowel gas 422, etc., may be identified by experienced operators, automatic real-time detection and visualization (or visual enhancement) of artifacts may simplify aiming of probe 110 and ensure better accuracy for both experienced and inexperienced operators. Detection and elimination of these artifacts in B-made images may also provide for more accurate C-mode images. Artifact identification unit 220 is described further, for example, in connection with FIG. 9.

Figure 7A:
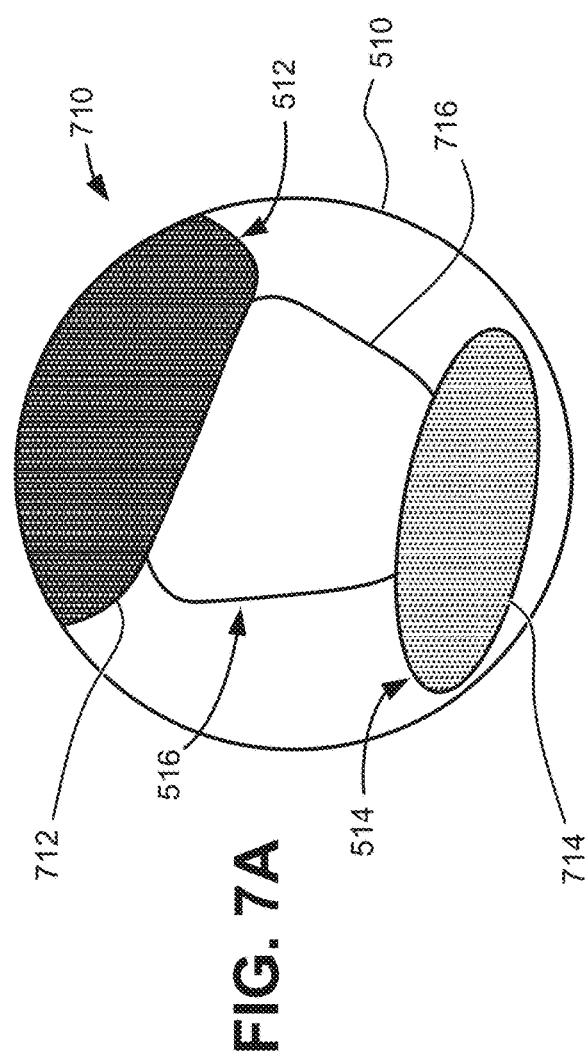
FIGS. 7A and 7B are sample visualizations applied to the C-mode images of FIGS. 5 and 5B.
Figure 7B:
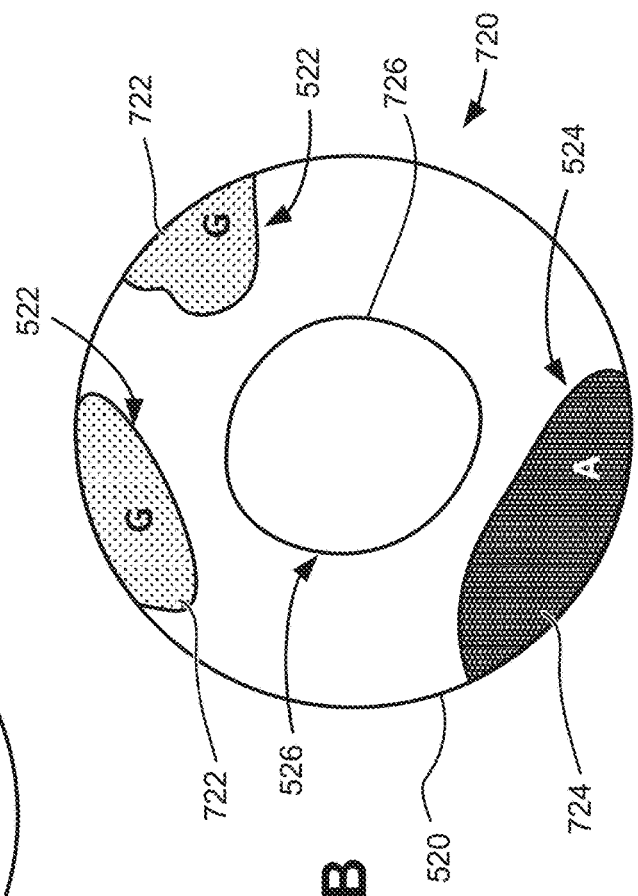

Returning to FIG. 2, visual indication generator 230 may apply a visual indication, such as an overlay on images, for artifacts detected by artifact identification unit 220. For example, based on a type of artifact detected by artifact identification unit 220, visual indication generator 230 may provide a highlight or outline of an artifact area. FIGS. 6A-7B provide examples of sample outputs that may be generated by visual indication generator 230. FIGS. 6A and 6B illustrate visualizations applied to B-mode images 410 and 420, respectively. FIGS. 7A and 7B illustrate visualizations applied to C-mode images 510 and 520 respectively.

Referring to FIG. 6A, visual indication generator 230 may provide an output 610 for a bladder scan. Output 610 may include B-mode image 410, an air artifact identifier 612, a shadow artifact identifier 614, and an organ outline 616. B-mode image 410 may correspond to echo data from one of scan planes 310 or 315 of FIG. 3A or 3B. Air artifact identifier 612 may be an outline, contrasting area, or another visible indicator highlighting air scan area 412 (e.g., as detected by artifact identification unit 220). Shadow artifact identifier 614 may be another outline, contrasting area, or different visible indicator highlighting pubic bone shadow 414. Organ outline 616 may correspond to an estimated shape of bladder 416 and may include another outline or visible indicator. In one implementation, air artifact identifier 612 and shadow artifact identifier 614 may be color-coded to indicate a respective type of artifact (e.g., air and shadow). In another implementation, artifact identifiers (including air artifact identifier 612, shadow artifact identifier 614, and other artifact identifiers described herein) may be supplemented with visible or audible text instructions to an operator. For example, a separate legend explaining the colors or artifact markings may accompany output 610.

As shown in FIG. 6A, the echo window for B-mode image 410 is partially blocked by the pubic bone (e.g., due to improper aim) and air (e.g., due to poor coupling). Bladder 416, in particular, is partially occluded by the pubic bone shadow 414, which means the estimated shape of bladder 416, as indicated by organ outline 616, may be inaccurate. Indicators 612, 614, and 616 of output 610 provide a clear visual indication of how artifacts (e.g., air scan area 412 and pubic bone shadow 414) can impact a desired target (e.g., bladder 416) measurement without complex processing heuristics or delays. Thus, indicators 612, 614, and 616 may provide an operator with real-time information that probe 110 adjustments are needed to obtain an accurate bladder scan.

Referring to FIG. 6B, visual indication generator 230 may provide an output 620 for an aorta scan. Output 620 may include B-mode image 420, a gas artifact identifier 622, and an organ outline 624. B-mode image 420 may correspond to echo data from one of scan planes 310 of FIG. 3A or scan planes 315 of FIG. 3B. Gas artifact identifier 622 may be an outline, contrasting area, or another visible indicator highlighting bowel gas area 422 (e.g., as detected by artifact identification unit 220). Organ outline 624 may correspond to an estimated shape of aorta 424 and may include another outline or indicator. Similar to artifact identifiers 612 and 614 described above, gas artifact identifier 622 may be color-coded and/or supplemented with descriptive text.

As shown in FIG. 6B, the echo window for B-mode image 420 is partially blocked by bowel gases. Aorta 424, however, is fully visible without obstruction. Indicators 622 and 624 of output 620 provide a clear visual indication that artifacts (e.g., bowel gas area 422) do not impact the desired target (e.g., aorta 424) measurement without the need for complex processing heuristics or delays. Thus, indicators 622 and 624 may provide an operator with real-time information that probe 110 adjustments are not needed to obtain an accurate scan.

Referring to FIG. 7A, visual indication generator 230 may provide an output 710 for a bladder scan. Output 710 may include C-mode image 510, an air artifact identifier 712, a shadow artifact identifier 714, and an organ outline 716. C-mode image 510 may correspond to echo data from C-mode image plane 320 of FIG. 3C. Air artifact identifier 712 may be an outline, contrasting color, or another visible indicator highlighting air scan area 512 (e.g., as detected by artifact identification unit 220). Shadow artifact identifier 714 may be another outline, contrasting color, or different visible indicator highlighting pubic bone shadow 514. Organ outline 716 may correspond to an estimated shape of bladder 516 and may include another outline, color, or indicator. In one implementation, air artifact identifier 712 and shadow artifact identifier 714 may be color-coded to indicate a respective type of artifact (e.g., air, shadow, etc.). In another implementation, artifact identifiers (including air artifact identifier 712, shadow artifact identifier 714, and other artifact identifiers described herein) may be supplemented with visible or audible text instructions to an operator.

As shown in FIG. 7A, the echo window for C-mode image 510 in general, and target bladder 516 in particular, is partially blocked by the pubic bone shadow (e.g., due to improper aim) and air (e.g., due to poor probe-skin coupling). Indicators 712, 714, and 716 of output 710 provide a clear visual indication of how the artifacts impede the desired target measurement (e.g., volume or size measurements of the bladder). Thus, indicators 712, 714, and 716 may provide an operator with real-time information that probe 110 adjustments are needed to obtain an accurate bladder scan.

Referring to FIG. 7B, visual indication generator 230 may provide an output 720 for an aorta scan. Output 720 may include C-mode image 520, gas artifact identifiers 722, air artifact identifier 724, and an organ outline 726. C-mode image 510 may correspond to echo data from C-mode image plane 320 of FIG. 3C. Gas artifact identifier 722 may be an outline, contrasting area, or another visible indicator highlighting bowel gas area 522 (e.g., as detected by artifact identification unit 220). Air artifact identifier 724 may be an outline, contrasting color, or another visible indicator highlighting air scan area 524 (e.g., as detected by artifact identification unit 220). Organ outline 726 may correspond to an estimated shape of aorta 526 and may include another outline or indicator. Similar to the other artifact identifiers described above, gas artifact identifier 722 may be color-coded and/or supplemented with descriptive text (e.g., "A" for air, "G" for gas, "S" for shadow, the words "air," "gas," "shadow," etc.).

As shown in FIG. 7B, a portion of the echo window for C-mode image 520 is blocked by air scan and bowel gases. Aorta 526, however, is visible without obstruction. Indicators 722, 724, and 726 of output 720 provide a clear visual indication that artifacts (e.g., bowel gas area 522 and air scan area 524) do not impact the desired target (e.g., aorta 526) measurement without the need for complex processing heuristics or associated delays. Thus, indicators 722, 724 and 726 may provide an operator with real-time information that probe 110 adjustments are not needed to obtain an accurate scan.

While FIGS. 6A-7B provide examples of visual artifact indicators for B-mode and C-mode scans for a bladder and aorta. In other implementations, visual indication generator 230 may provide an output with visual indicators for artifacts in other scan modes and/or for other target objects.

Referring again to FIG. 2, main processing logic 240 may provide additional analysis of a target object (e.g., bladder 416, aorta 424, etc.), such as cavity-type recognition, volume estimations, diameter or size estimations, or other clinically useful information with B-mode, C-mode, or other types of images acquired by data acquisition unit 210. For example, main processing logic 240 may identify a cavity as a bladder, estimate a volume for the bladder, or identify a diameter of the aorta.

The exemplary configuration illustrated in FIGS. 1 and 2 is provided for simplicity. System 100 may include more or fewer logic units/devices than illustrated in FIGS. 1 and 2. For example, system 100 may include multiple data acquisition units 210 and multiple processing units that process the received data. In addition, system 100 may include additional elements, such as communication interfaces (e.g., radio frequency transceivers) that transmit and receive information via external networks to aid in analyzing ultrasound signals to identify a target object of interest. Furthermore, while illustrations and descriptions herein primarily refer to bladder and aorta applications, other embodiments can be applied to wall boundary detection of other organs, such as a prostate/kidney boundary, other blood vessels, thyroid, etc.

Figure 8:
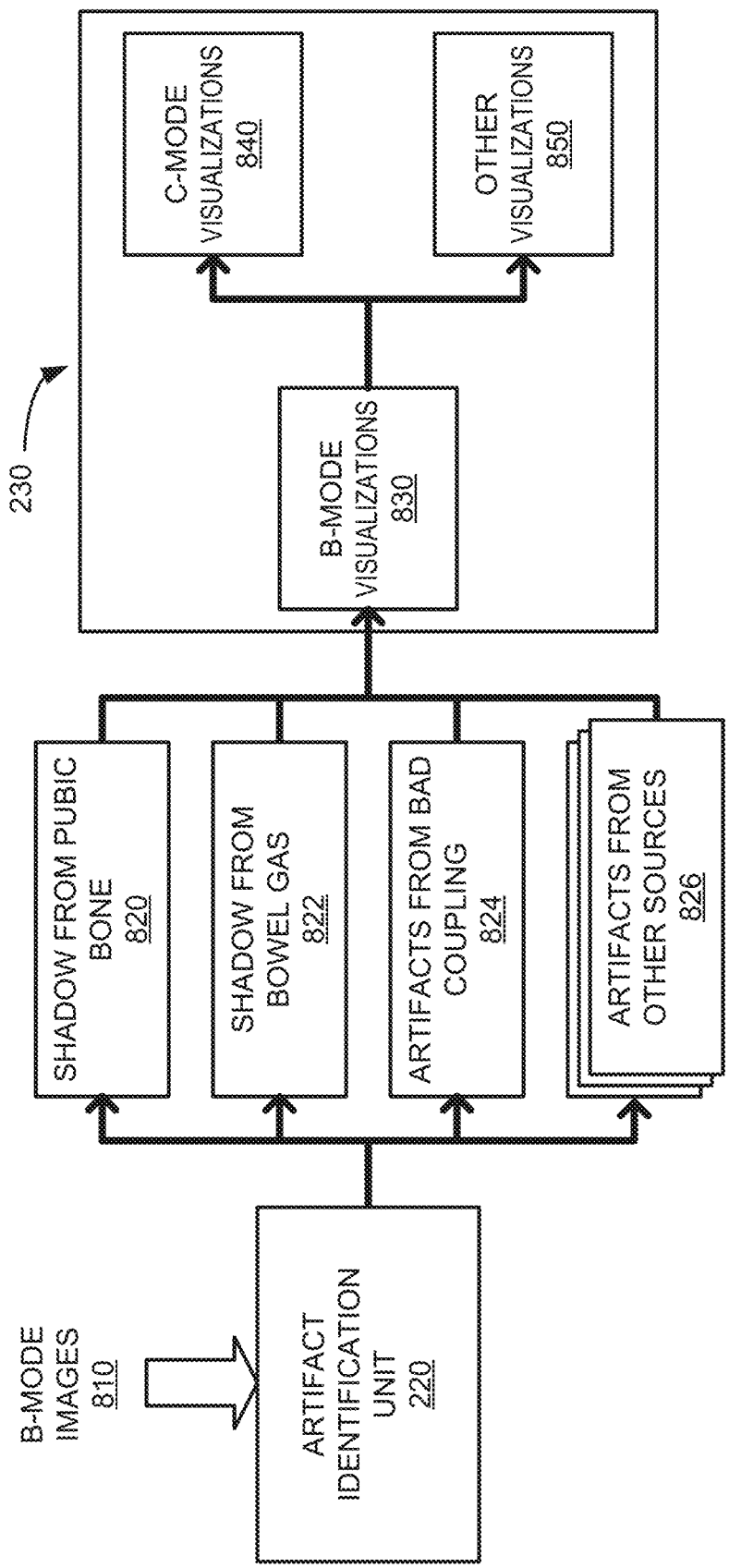
FIG. 8 is a block diagram illustrating communications between functional logic components in the scanning system of FIG. 1.

FIG. 8 is a block diagram illustrating communications between functional logic components in scanning system 100. As shown in FIG. 8, B-mode images 810 (e.g., from data acquisition unit 210) may be received by artifact identification unit 220, which may detect features of pixels and/or pixel grouping within each B-mode image 810 to permit artifact classification.

Artifact identification unit 220 may associate artifact portions (e.g. pixels) of the B-mode image 810 into one or more classes based on criteria from training data. In one implementation, artifact identification unit 220 may apply a pre-trained deep convolutional neural network (DCNN). A DCNN or other image classification algorithms may be well-suited for application of hardwired circuitry, such as a field-programmable gate array (FPGA), an application specific integrated circuits (ASIC), etc., to provide rapid image classification. Each type of artifact may result in distinct types of pixel groupings within an ultrasound image that can be detected using probability matching. According to one example, artifact identification unit 220 may include a probability map corresponding to the different types of shadows (e.g., strong shadows from pubic bone versus lighter shadows from bowel gas) and other artifacts (reverberations due to poor probe-to-skin coupling) inside B-mode images. In one implementation, artifact definitions may be generated off-line by a machine learning system and stored in artifact identification unit 220. In another implementation, artifact identification unit 220 may include a dynamic learning capability, where actual processed images and user responses to visualizations (e.g., visualizations 612, 712, etc.) may be used improve artifact identification unit 220.

In the example of FIG. 8, artifact identification unit 220 may use four different classes: shadow from public bone 820, shadow from bowel gas 822, artifacts from bad coupling 824, and artifacts from other sources 826. Shadow from public bone 820, shadow from bowel gas 822, artifacts from bad coupling 824 may represent primary known artifact classes that are detectable from pixel groupings in B-mode images. Artifacts from other sources 826 may include any unidentified artifact or other types of known artifacts not in the primary known artifact classes, such as a catheter or needle shadow class, a rib shadow class, or other classes which impact the scanning image quality and associated quantitative analysis accuracy. In one implementation, artifacts from other sources 826 may be separated into multiple classes or sub-classes, such as separate groupings for catheter or needle shadow class, a rib shadow class, and an unknown class. In some cases, pixels may be classified under multiple classes. Artifact identification unit 220 may support any number of categories for output, as long as the amount of ultrasound images in the training dataset supports each category. However, as the total number of categories grows, the classification distance (e.g., in terms of image feature space) between two categories could be potentially decreased, which could lead to difficulties for the correct classification and the confusion to human operators. In one implementation, artifact identification unit 220 may use no more than six categories.

The particular artifact classes 820, 822, 824, and 826 shown in FIG. 8 may be appropriate for a particular ultrasound application, such as conducting a bladder scan. In other implementations, different types or amounts of artifact classes may be used in artifact identification unit 220. For example, for an abdominal aortic aneurysm (AAA) scan, artifacts from bad coupling and shadow from bowel gas may be the primary classes with an undefined (or "other sources") class for other artifacts. Conversely, for a new type of human heart scan, shadows from ribs and shadows from medical devices may be two primary artifact classifications (e.g., instead of being grouped together in an "other sources" class).

Artifact identification unit 220 may forward locations and classes of classified pixels to visual indication generator 230. Visual indication generator 230 may produce overlays corresponding to the location and class of the artifact pixels. A B-mode visualizations unit 830 may apply visualizations (e.g., air artifact identifier 612, gas artifact identifier 622, etc.) directly to B-mode images. For C-mode images, a C-mode visualizations unit 840 may receive and compile locations for B-mode visualizations with other B-mode data to generate C-mode visualizations (e.g., air artifact identifier 712, gas artifact identifier 722, etc.). For other types of images, such as three-dimensional renderings, other visualizations unit 850 may receive and compile locations of B-mode visualizations with other image data to generate the other types of ultrasound images.

Figure 9:
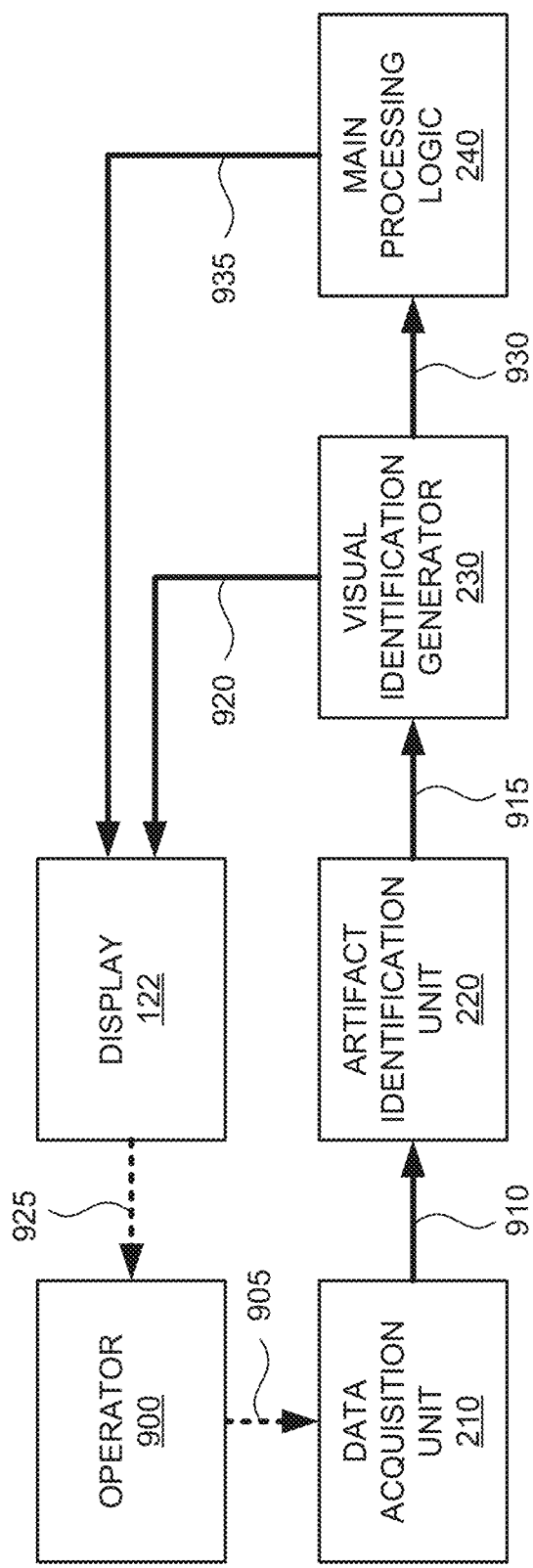
FIG. 9 is a block diagram of exemplary communications for classifying echo window artifacts and generating visual indicators in the scanning system of FIGS. 1 and 2.

FIG. 9 is a block diagram of exemplary communications for generating real-time artifact visualizations in scanning system 100. An operator 900 may use ultrasound probe 110 to acquire real-time data from a targeted anatomical region. For example, operator 900 may control probe 110 to position 905 the nose of probe 110 toward an organ of interest (e.g., organ 152 of FIG. 1) and emit ultrasonic signals.

Data acquisition unit 210 may receive echo data and process the echo data to generate, for example, a two-dimensional B-mode image 910. Data acquisition unit 210 may forward B-mode image 910 to artifact identification unit 220.

Artifact identification unit 220 may analyze image 910 using, for example, a multi-class artifact categorization algorithm to classify different areas (e.g., pixels) of image 910 with one or more of multiple different artifact categories, such as an air scan area 412, a pubic bone shadow 414, etc. According to an implementation, pixels of image 910 may be simultaneously included in two separate categories. For example, artifact identification unit 220 may identify some pixels in image 910 as having both strong shadows and reverberations. Artifact identification unit 220 may forward the category associations 915 for pixels of image 910 to visual indication generator 230.

Visual indication generator 230 may receive category associations 915 and generate artifact visualizations based on category associations 915. According to an implementation, visual indication generator 230 may match the category associations 915 to a particular color, indication, and/or textual reference using a table.

Visual indication generator 230 may select appropriate visualizations/text corresponding to the category for pixels in image 910 and submit an enhanced image 920 (e.g., output 610, 620, etc.) to display 122 for presentation to operator 900. The artifact visualizations (e.g., gas artifact identifier 622, etc.) may be displayed on the screen (e.g., display 122) and, optionally, audibly output by a speaker to provide the operator real-time feedback and instructions in helping the operator acquire best quality data and subsequently accurate calculated results, such as volume or size measurements.

Because artifact identification unit 220 analyzes individual B-mode images (e.g., two-dimensional images), enhanced image 920 from visual indication generator 230 may be presented (via display 122) in real-time (e.g., less than 0.5 seconds delay). Artifact visualizations for C-mode images, which are generated from the B-mode visualizations, may be similarly presented without significant delay.

Operator 900 may detect 925 enhanced image 920 from display 122. Assuming enhanced image 920 includes artifact visualizations that require a user to adjust probe 110, operator 900 may re-position 905 probe 110 (or take other actions to correct artifacts). Data acquisition unit 210 may receive new echo data and process the new echo data to generate another B-mode image 910, C-mode image, etc. Artifact identification unit 220 may analyze the image 910 for artifact pixels to again provide category associations 915 to visual indication generator 230.

Assuming enhanced image 920 includes artifact visualizations that do not obstruct a target object, operator 900 may choose to not adjust probe 110. Visual indication generator 230 may forward the unobstructed/accepted image 930 to main processing logic 240.

Main processing logic 240 may receive image 930 and subsequent images 930, if needed, to provide a desired measurement or calculation, such as an organ boundary, bladder volume estimate, cavity recognition, aorta size, etc., based on image 930. Main processing logic 240 may provide a calculated result 935 to display 122 for presentation to the operator 900.

Figure 10:
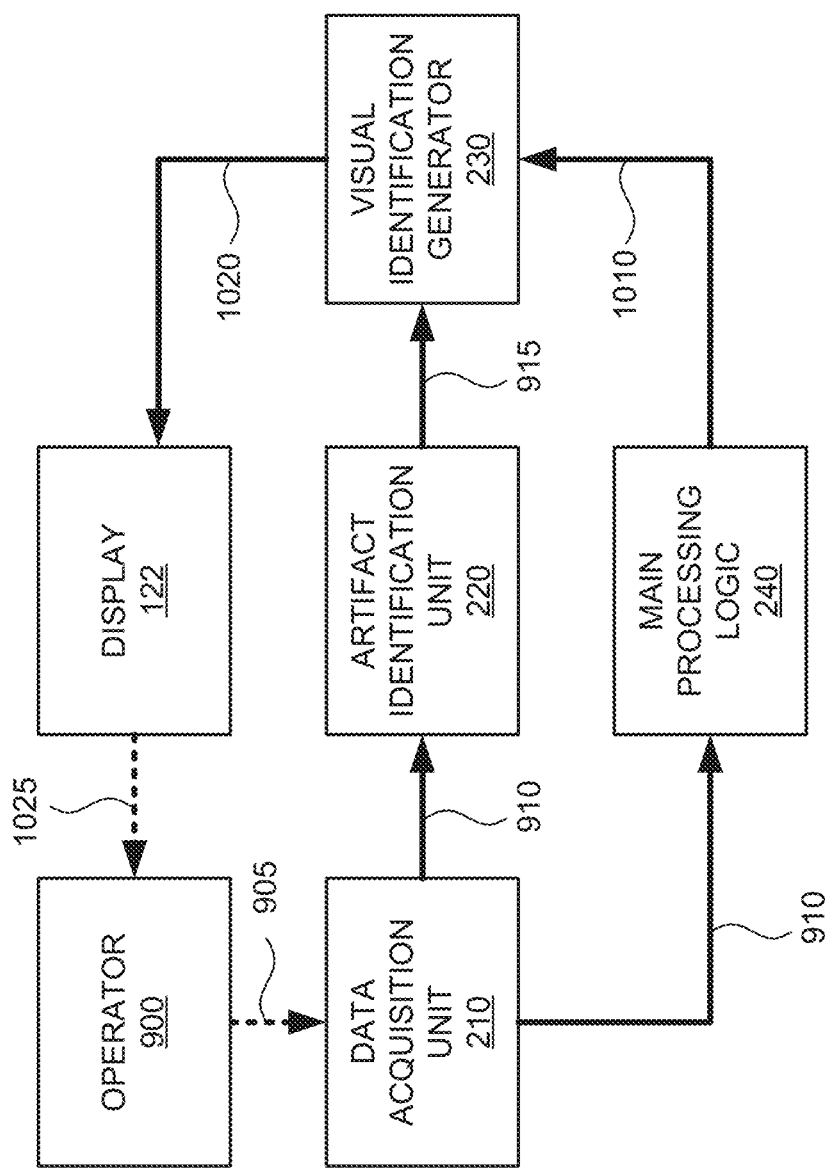
FIG. 10 is a block diagram of exemplary communications for classifying echo window artifacts and generating visual indicators, according to another embodiment, in the scanning system of FIGS. 1 and 2.

FIG. 10 is a block diagram of exemplary communications for generating real-time artifact visualizations in scanning system 100 according to another implementation. Communications in FIG. 10 represent feedback provided to an operator along with a requested output.

Similar to communications described in connection with FIG. 9, in FIG. 10, operator 900 may control probe 110 to position 905 the nose of probe 110 toward an organ of interest and emit ultrasonic signals. Data acquisition unit 210 may receive echo data and process the echo data to generate image 910. Data acquisition unit 210 may send image 910 to artifact identification unit 220. Artifact identification unit 220 may analyze image 910 and classify pixel groupings or areas within image 910 into one or more artifact categories. Artifact identification unit 220 may provide category associations 915 for image 910 to visual indication generator 230.

Additionally (and simultaneously) with sending image 910 to artifact identification unit 220, data acquisition unit 210 may send image 910 to main processing logic 240. Main processing logic 240 may receive image 910 and subsequent images 910, if needed, to detect a target object (e.g., a bladder, kidney, aorta, medical device, etc.) and provide a desired measurement or calculation, such as an organ boundary/shape or a bladder volume estimate, based on image 910. Thus, an artifact assessment (from artifact identification unit 220) and a calculated measurement (from main processing logic 240) can be obtained at the same time. Main processing logic 240 may provide the calculated result 1010 to visual indication generator 230.

Visual indication generator 230 may receive category associations 915 and calculated results 1010. Visual indication generator 230 may use category associations 915 and calculated results 1010 to generate a visualization of artifact areas for operator 900. In one implementation, visual indication generator 230 may provide the calculated result 1010 with additional guidance to indicate a potential error in a calculated result due to the presence of artifacts.

Visual indication generator 230 may select appropriate visualizations corresponding to the class of artifacts detected within image 910 and submit the images with artifact visualizations as output 1020 to display 122 for presentation to operator 900. For example, output 1020 may correspond to output 610, 620, 710, or 720, described above and may be presented via display 122. Operator 900 may detect 1025 output 1020 on display 122. Operator 900 can choose to adjust probe 110 and re-scan or simply accept the result based on the location of the target object relative to the visualized artifacts (if any).

Figure 11:
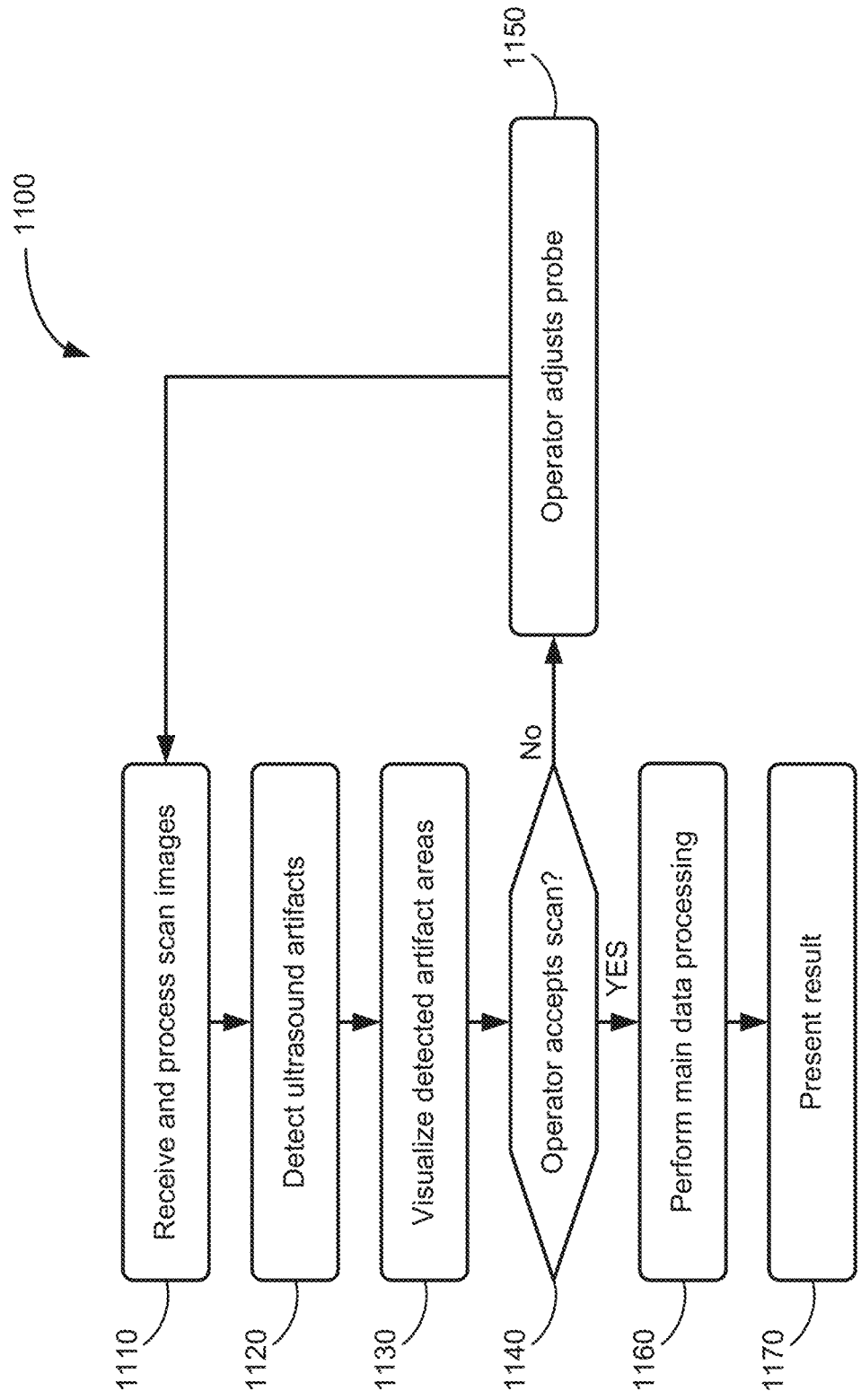
FIG. 11 is a process flow diagram for providing artifact detection and visualization during ultrasound image collection.

FIG. 11 is a flow diagram illustrating an exemplary process 1100 for generating real-time artifact visualizations for ultrasound scans. Process 1100 may be performed, for example, by base unit 120 of system 100. In another implementation, process 1100 may be performed by base unit 120 in conjunction with probe 110. In one implementation, process 1100 may begin after probe 110 obtains an ultrasound image as described above.

Process 1100 may include receiving and processing scan images (block 1110). For example, data acquisition unit 210) may receive one or more B-mode ultrasound image from probe 110 and apply noise reduction and/or other pre-processing techniques to remove speckle and background noise from the image. In some embodiments, the aspect ratio of the raw B-mode image can be adjusted through a resizing process to compensate for differences between axial and lateral resolution. In other implementations, such as bladder scanning applications, a scan conversion can also be applied to make a bladder shape more accurately reflect the actual shape of a typical bladder.

Process 1100 may also include detecting ultrasound artifacts in the scan images (block 1120) and visualizing the detected artifact areas (block 1130). For example, artifact identification unit 220 may receive pre-processed images, such as image 910, from data acquisition unit 210. Artifact identification unit 220 may analyze pixel groupings in image 910 using, for example, a multi-class image categorization algorithm to classify areas of image 910 into one or more of multiple different artifact categories (e.g., pubic bone shadow, bowel gas shadow, reverberations, etc.). Visual indication generator 230 may generate visible indicators for the different types of artifacts in real time and overlay the artifact visualizations over the scan image for presentation to the operator 900.

The operator may decide to accept the scan (block 1140). For example, based on the location of visualized artifacts relative to a target object, operator 900 may determine that a scan is acceptable despite the presence of ancillary artifacts. Alternatively, operator 900 may determine that artifacts (e.g., as represented by visualizations 612, 712, etc.) require probe adjustment and re-scanning.

If the operator does not accept the scan (block 1140—NO), process 1100 may include the operator adjusting the probe (block 1150) and returning to block 1110 to receive and process scan images. For example, operator 900 may reject a scan with output (e.g. output 610, 710) that shows artifacts occluding a target object. Operator 900 may adjust the probe 110 position, apply more gel to the skin, or take other corrective actions to improve the scan result and initiate another scan.

If the operator accepts the scan (block 1140—YES), process 1100 may include performing main processing (block 1160) and presenting a result (block 1170). For example, operator 900 may accept a scan with no artifacts or output (e.g. output 620, 720) that shows artifacts in the echo window do not impact view of a target object. Main processing logic 240 may perform a request calculation/measurement for the target object and return a result (e.g., bladder volume, aorta diameter, etc.) to operator 900.

Although FIG. 11 shows a particular order of blocks for process 1110, in other implementations, process 1100 may be performed in a different order. For example, in one implementation, the main data processing of block 1160 may be performed simultaneously with blocks 1120 and/or 1130.

FIG. 12 is a diagram illustrating exemplary physical components of base unit 120. Base unit 120 may include a bus 1210, a processor 1220, a memory 1230, an input component 1240, an output component 1250, and a communication interface 1260. In other implementations, probe 110 may include similar components.

Bus 1210 may include a path that permits communication among the components of base unit 120. Processor 1220 may include a processor, microprocessors, ASICs, controllers, programmable logic devices, chipsets, FPGAs, graphics processing unit (GPU), application specific instruction-set processors (ASIPs), system-on-chips (SoCs), central processing units (CPUs) (e.g., one or multiple cores), microcontrollers, and/or some other type of component that interprets and/or executes instructions and/or data. Processor 1220 may be implemented as hardware (e.g., an FPGA, etc.), a combination of hardware and software (e.g., a SoC, an ASIC, etc.), may include one or multiple memories (e.g., cache, etc.), etc.

Memory 1230 may include any type of dynamic storage device that may store information and instructions (e.g., software 1235), for execution by processor 1220, and/or any type of non-volatile storage device that may store information for use by processor 1220.

Software 1235 includes an application or a program that provides a function and/or a process. Software 1235 is also intended to include firmware, middleware, microcode, hardware description language (HDL), and/or other form of instruction.

Input component 1240 may include a mechanism that permits an operator to input information to base unit 120, such as a keyboard, a keypad, a button, a switch, a touch screen, etc. Output component 1250 may include a mechanism that outputs information to the operator, such as a display (e.g., display 122), a speaker, one or more light emitting diodes (LEDs), etc.

Communication interface 1260 may include a transceiver that enables base unit 120 to communicate with other devices and/or systems via wireless communications, wired communications, or a combination of wireless and wired communications. For example, communication interface 1260 may include mechanisms for communicating with another device or system, such as probe 110, via a network, or to other devices/systems, such as a system control computer that monitors operation of multiple base units (e.g., in a hospital or another type of medical monitoring facility). In one implementation, communication interface 1260 may be a logical component that includes input and output ports, input and output systems, and/or other input and output components that facilitate the transmission of data to/from other devices.

Base unit 120 may perform certain operations in response to processor 1220 executing software instructions (e.g., software 1235) contained in a computer-readable medium, such as memory 1230. A computer-readable medium may be defined as a non-transitory memory device. A non-transitory memory device may include memory space within a single physical memory device or spread across multiple physical memory devices. The software instructions may be read into memory 1230 from another computer-readable medium or from another device. The software instructions contained in memory 1230 may cause processor 1220 to perform processes described herein. Alternatively, hardwired circuitry, such as an ASIC, an FPGA, etc., may be used in place of or in combination with software instructions to implement processes described herein. Thus, implementations described herein are not limited to any specific combination of hardware circuitry and software.

Base unit 120 may include fewer components, additional components, different components, and/or differently arranged components than those illustrated in FIG. 12. As an example, base unit 120 may include one or more switch fabrics instead of, or in addition to, bus 1210. Additionally, or alternatively, one or more components of base unit 120 may perform one or more tasks described as being performed by one or more other components of base unit 120.

Systems and methods described herein provide real-time artifact visualizations to operators during the ultrasound scanning. The real-time artifact visualization is helpful in assisting inexperienced operators, as well as experienced operators, to acquire high quality ultrasound data and achieve accurate calculated organ dimensions, such as bladder volume measurements, aorta diameter, etc. Machine learning, such as a deep convolutional neural network, enables rapid classification of artifact areas within scan images that can be used to provide real-time feedback.

Systems and methods described herein minimize the requirement for an operator to interpret artifacts within ultrasound images and transfer that task to logic within system 100. Conventional ultrasound systems require that an operator interpret image content or wait for complete scan results to determine if artifacts have impacted the scan results. For inexperienced users, correctly understanding what happens in an ultrasound image is not a trivial task. The systems and methods described herein perform an initial level of artifact detection for the operators to minimize the burden of image interpretation and delays of a full scan calculation before detecting probe operator errors.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A method, comprising:
   receiving, by a processor associated with an ultrasound probe, ultrasound image data
   that includes a target object and areas with artifacts, wherein the areas with artifacts are classified into one of a plurality of known artifact classes;
   generating, by the processor, an indication of the areas with artifacts for an ultrasound-based image, wherein the indications include an overlay with a designation of the artifact class; and
   presenting, to an operator of the ultrasound probe and via a display screen, an enhanced ultrasound-based image including the indication of the areas with artifacts relative to a target object and the designation of the artifact class associated with each artifact.

2. The method of claim 1, wherein the ultrasound image data includes a two-dimensional B-mode image.

3. The method of claim 1, wherein the ultrasound image data includes multiple B-mode images.

4. The method of claim 2, wherein the presenting includes presenting the enhanced ultrasound-based image as a C-mode image based on a compilation of the multiple B-mode images.

5. The method of claim 1, wherein the plurality of known artifact classes include a pubic bone shadow class, a bowel gas shadow class, and a bad coupling class.

6. The method of claim 1, wherein the presenting further includes presenting a result for the target object and guidance to indicate a potential error in the result due to the presence of the artifacts.

7. The method of claim 1, wherein the artifacts are classified into one of a plurality of known artifact classes
   based on pixel groupings in training images with previously-recognized artifact types.

8. The method of claim 1, wherein the presenting further comprising:
   providing audible instructions to an operator.

9. The method of claim 1, wherein the presenting includes providing descriptive text within the enhanced ultrasound image.

10. The method of claim 1, wherein the target object is an organ including one of a bladder, an aorta, a prostate, a kidney, a blood vessel, or a thyroid.

11. A device, comprising:
    a memory device for storing instructions; and
    a processor configured to:
       receive ultrasound image data
       that includes a target object and areas with artifacts, wherein the areas with artifacts are classified into one of a plurality of known artifact classes,
       generate an indication of the areas with artifacts for an ultrasound-based image, wherein the indications include an overlay with a designation of the artifact class, and
       present, to an operator of the ultrasound probe and via a display screen, an enhanced ultrasound-based image including the indication of the areas with artifacts relative to a target object and the designation of the artifact class associated with each artifact.

12. The device of claim 11, wherein the ultrasound image data includes a two-dimensional B-mode image.

13. The device of claim 11, wherein, when presenting the enhanced ultrasound-based image, the processor is further configured to present the enhanced ultrasound-based image as a C-mode image based on a compilation of the multiple B-mode images.

14. The device of claim 11, wherein the plurality of known artifact classes include a pubic bone shadow class, a bowel gas shadow class, and a bad coupling class.

15. The device of claim 11, wherein, when presenting the enhanced ultrasound-based imam the processor is further configured to:
    present a result for the target object and guidance to indicate a potential error in the result due to the presence of the artifacts.

16. The device of claim 11, wherein the processor is further configured to:
  generate an indication of a target object within the enhanced ultrasound image; and
  calculate a result based on the indication of the target object.

17. The device of claim 11, wherein, when presenting the enhanced ultrasound-based image, the processor is further configured to:
  provide descriptive text within the enhanced ultrasound image.

18. A non-transitory computer-readable medium containing instructions executable by at least one processor, the computer-readable medium comprising one or more instructions to:
  receive ultrasound image data
  that includes a target object and areas with artifacts, wherein the areas with artifacts are classified into one of a plurality of known artifact classes,
  generate an indication of the areas with artifacts for an ultrasound-based image, wherein the indications include an overlay with a designation of the artifact class, and
  present, to an operator of the ultrasound probe and via a display screen, an enhanced ultrasound-based image including the indication of the areas with artifacts relative to a target object and the designation of the artifact class associated with each artifact.

19. The non-transitory computer-readable medium claim 18, wherein the known artifact classes include a pubic bone shadow class, a bowel gas shadow class, and a bad coupling class.

20. The non-transitory computer-readable medium claim 19, wherein the instructions to present the an enhanced ultrasound-based image further comprise one or more instructions to:
  present a calculated result for the target object and guidance to indicate a potential error in the calculated result due to the presence of the artifacts.

* * * * *